US012694988B2

(12) United States Patent
Lam et al.

(10) Patent No.: US 12,694,988 B2
(45) Date of Patent: Jul. 28, 2026

(54) COMPUTER-IMPLEMENTED METHOD FOR CREATING A FUNCTIONAL FORM, DATA PROCESSING SYSTEM AND COMPUTER-READABLE MEDIUM

(71) Applicant: Ottobock SE & Co. KGaA, Duderstadt (DE)

(72) Inventors: Khoi Lam, Munich (DE); Max Thalmeier, Munich (DE)

(73) Assignee: Ottobock SE & Co. KGaA, Duderstadt (DE)

( * ) Notice: Subject to any disclaimer, the term of this patent is extended or adjusted under 35 U.S.C. 154(b) by 1102 days.

(21) Appl. No.: 17/635,162

(22) PCT Filed: Aug. 14, 2019

(86) PCT No.: PCT/EP2019/071824

§ 371 (c)(1),
(2) Date: Feb. 14, 2022

(87) PCT Pub. No.: WO2021/028038

PCT Pub. Date: Feb. 18, 2021

(65) Prior Publication Data

US 2022/0277856 A1     Sep. 1, 2022

(51) Int. Cl.
*G16H 50/50*          (2018.01)
(52) U.S. Cl.
CPC .................................. *G16H 50/50* (2018.01)
(58) Field of Classification Search
CPC ...................................................... G16H 50/50
See application file for complete search history.

(56) References Cited

U.S. PATENT DOCUMENTS

| | | | |
|---|---|---|---|
| 9,402,726 B2 | 8/2016 | Linderman et al. | |
| 2019/0021880 A1* | 1/2019 | Herr ........................... | A61F 2/60 |
| 2021/0137634 A1* | 5/2021 | Lang ....................... | A61B 90/00 |

FOREIGN PATENT DOCUMENTS

| | | | | |
|---|---|---|---|---|
| CN | 105474219 A | 4/2016 | | |
| DE | 202004020415 U1 * | 10/2005 | ........... | A61F 2/5046 |
| EP | 2359288 B1 | 6/2019 | | |
| EP | 3534279 A2 | 9/2019 | | |
| EP | 3534279 A3 | 9/2019 | | |
| WO | 2010140036 A1 | 12/2010 | | |

OTHER PUBLICATIONS

Patent Cooperation Treaty: International Search Report and Written Opinion for PCT/EP2019/071824; Pedro V. Rivera; April 77, 2020; 17 pages.

* cited by examiner

*Primary Examiner* — Bijan Mapar
(74) *Attorney, Agent, or Firm* — Goodwin Procter LLP

(57)          ABSTRACT

The invention refers to a computer-implemented method for creating a functional form, in particular as a basis for individually fitting an orthosis or prosthesis to a first patient, comprising the steps of receiving of anatomic structural data (ASD) of the first patient and applying a transfer algorithm to generate functional form data (FFD) for the first patient, whereby the received functional form data (FFD) forms the basis on which an individualized orthosis or prosthesis is manufactured. Furthermore, the invention refers to a data processing system and a computer-readable medium.

14 Claims, 1 Drawing Sheet

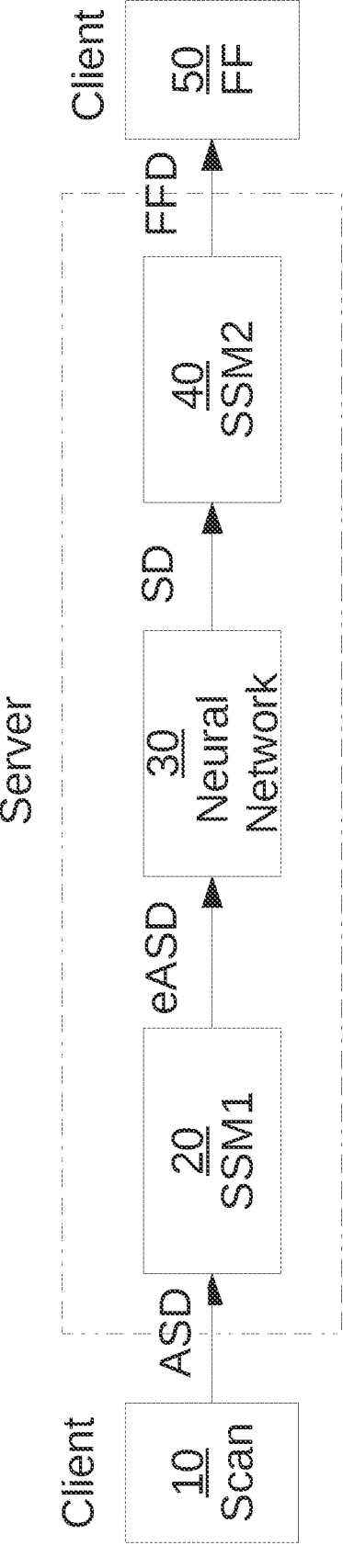

COMPUTER-IMPLEMENTED METHOD FOR CREATING A FUNCTIONAL FORM, DATA PROCESSING SYSTEM AND COMPUTER-READABLE MEDIUM

CROSS-REFERENCE TO RELATED APPLICATIONS

This application is a U.S. National Phase application submitted under 35 U.S.C. § 371 of Patent Cooperation Treaty application serial no. PCT/EP2019/071824, filed Aug. 14, 2019, and entitled COMPUTER-IMPLEMENTED METHOD FOR CREATING A FUNCTIONAL FORM, DATA PROCESSING SYSTEM AND COMPUTER-READABLE MEDIUM, published as WO 2021/028038 A1, the specification of which is incorporated herein.

TECHNICAL FIELD

The invention refers to a computer-implemented method for creating a functional form, in particular as a basis for individually fitting an orthosis or prosthesis to a first patient. Moreover, the invention refers to a data processing system and a computer-readable medium.

BACKGROUND

Usually, an orthosis or a prosthesis is individually manufactured and modified for a patient step by step. For this purpose, a functional form can be created which substitutes the patient's extremity for fitting of the orthosis or prosthesis. In particular, e.g. a certified prosthetist/orthotist and/or an orthopaedic technician manually adapts the orthosis or prosthesis on basis of the extremity of the patient itself, for example of the lower leg, or on basis of a functional form thereof. A digital illustration of the visualization of a three-dimensional structure of the scan data/the anatomic structural data of the patient or of the respective functional form can be of further assistance for the certified prosthetist/orthotist and/or the orthopaedic technician in this regard.

Nevertheless, such manual preparation and adaption of a patient specific orthosis or prosthesis not only necessitates time and thus is expensive, but also requires an extensive education and background knowledge by the certified prosthetist/orthotist and/or the orthopaedic technician, not only regarding the professional expertise but also with respect to the handling of appropriate software. Thus, certified prosthetists/orthotists and/or the orthopaedic technicians have to undergo additional training courses nowadays to handle usual working processes, in particular including different kinds of software programmes, for creating individually adapted orthosis or prosthesis digitally.

SUMMARY

The object of the invention is to provide an improved method for providing a basis for individually fitting an orthosis or prosthesis, which are individually adapted and manufactured for the respective patient, whereby the process is time efficient as well as cost efficient, easy to handle and reduces the amount of background knowledge and education being necessary to provide such an individual orthosis or prosthesis. Furthermore, it is an object of the invention to provide a data processing system and a computer-readable medium.

The present invention solves these problems by providing a computer-implemented method according to claim 1, as well as a data processing system according to independent claim 11 and a computer-readable medium according to claim 13. Further preferred embodiments of the invention are described by the dependent claims respectively.

According to the present invention a computer-implemented method for creating a functional form, in particular as a basis for individually fitting an orthosis or prosthesis to a first patient, is provided, which comprises the following steps:

a) receiving of anatomic structural data of the first patient;

b) applying a transfer algorithm to generate functional form data for the first patient;

whereby the received functional form data forms the basis on which an individualized orthosis or prosthesis is manufactured.

The present invention is based on the idea to provide a functional form for the patient's anatomy, in particular of an extremity such as a lower leg, as a basis for fitting the orthosis or prosthesis in advance to its manufacturing. Thereby, creation of the patient specific functional form is automatized by utilization of a transfer algorithm being capable of transferring the patient's scan data to finally achieve a functional form.

By automating the process for achieving at least a first rough functional form time and financial resources can be saved. Furthermore, additional background knowledge of the respective certified prosthetist/orthotist and/or orthopaedic technician for creating such a functional form can be reduced, in particular with regard to software handling etc.

In the sense of the present invention the functional form represents an adapted or optimized geometry of the patient's anatomy, such as a lower leg, in order to appropriately fit an orthosis or prosthesis. Preferably, the functional form or functional form data is not exactly identical with the scan data/anatomic structural data of the first patient but diverge in order to provide a suitable fitting of the resulting orthosis or prosthesis.

Further, according to the present invention the transfer algorithm is capable of transferring data which can be further processed to finally achieve functional form data. Thus, the transfer algorithm can provide any appropriate format of data, in particular structural data which can be converted to functional form data in order to provide a functional form.

In a preferred embodiment step b) comprises encoding the anatomic structural data, preferably by means of a first statistical shape model.

According to another preferred embodiment the first statistical shape model encodes the anatomic structural data in form of deviations of the anatomic structural data of the first patient from anatomic structural data of a limited amount of various patients as comprised by the first statistical shape model, in particular in form of encoded anatomic structural data of the limited amount of various patients.

In the sense of the present invention, data as processed by a statistical shape model can refer to statistical deviations or the like, in particular to compress the amount of data being stored and/or processed. By applying statistical shape models different approaches to reduce or compress data, in particular the scan data/anatomic structural data, can be used. For example, statistical deviations/differences of the first patient's data in comparison to the data of a limited amount of patients can be utilized. In particular, such statistical deviations can be focused on a specific number of characteristic landmark points of an extremity of the first patient.

In one embodiment, a statistical shape model comprises the average positions of the landmark points and has a number of parameters which control the main modes of variation found in the data of the limited amount of various patients. Each spatial axis of the three-dimensional data gives a mode of variation to describe in which way the landmark points tend to move together as the shape varies. Thus, the mode of variation of the data of one single patient refer to the difference from the mean value of all data of the limited amount of various patients.

The first statistical shape model provides mean positions and variations of the anatomic structural data of the various patients, whereby a second statistical shape model provides mean positions and variations of landmark points along the functional form data of the various patients. Thus, in the sense of the present invention the statistical shape models refer to statistical deviations between the data of patients, in particular between landmark points of the different anatomic structural data and/or the structural data of various patients.

In particular, the first statistical shape model is provided with/comprises anatomic structural data of multiple various patients in order to provide means and deviations in form of encoded anatomic structural data. The second statistical shape model is provided with/comprises functional form data of multiple various patients in order to provide means and deviations in form of structural data. Thus, the first and second statistical shape models comprise data pairs, in particular of the limited amount of various patients.

In this regard, the encoded anatomic structural data of the first patient can be provided by the first statistical shape model, namely as an object preferably comprising mean positions of the landmark points according to the anatomic structural data of the limited amount of various patients in combination with modes of variation for the first patient. Further, an arbitrary amount of characteristic landmark points being manually or automatically defined on the anatomic structural data of the limited amount of different patients and of the first patient can be used, e.g. a maximum of 30, 25, 20, 15, 10, 5 or 3 landmark points.

By using statistical shape models for the transformation of anatomic structural data in order to achieve functional form data, compressed data are provided. Thus, the handling of these encoded/compressed anatomic structural data by the transfer algorithm is optimized by reducing the amount of data, in particular to relevant and/or significant information.

Furthermore, it is of advantage to use as less data as possible, e.g. as less landmark points as possible, due to the correlation of an increasing amount of characteristic parameter with the increasing amount of necessary data of various other patients, as comprised by the statistical shape models. Thus, a large amount of e.g. landmark points will necessitate more data of different patients for training/adapting the transfer algorithm and will result in longer processing times consequently.

In one embodiment of the present invention step b) further comprises decoding the structural data as provided by the transfer algorithm, to receive functional form data, preferably by means of a second statistical shape model.

In another embodiment the second statistical shape model decodes the structural data of the first patient representing deviations from functional form data of a limited amount of various patients as comprised by the second statistical shape model, in particular in form of structural data of the various patients, to provide functional form data for the first patient.

The transfer algorithm can supply structural data in form of a second object with mean positions in combination with modes of variation. Thus, the data as comprised by the second statistical shape model refer to a functional form, in particular to mean positions and modes of variations of landmark points which are defined along the functional form.

In particular, the process of decoding the structural data can be considered as some kind of reverse action of the encoding process by the first statistical shape model in order to provide suitable functional form data/a suitable functional form.

The second statistical shape model decodes structural data as provided by the transfer algorithm to achieve functional form data. This decoding process by the second statistical shape model can further be considered as a decompression/regeneration of data information, in comparison to the process of data compression by the first statistical shape model.

According to another embodiment step b) further comprises:

applying the transfer algorithm, in particular using a neural network, to the anatomic structural data of the first patient as comprised by the first statistical shape model, in particular to the encoded anatomical structural data of the first patient.

Thus, the transfer algorithm further processes the patient's individual data as encoded and provided by the first statistical shape model. Namely, the compressed/encoded anatomic structural data of the first patient are transferred/converted by the transfer algorithm to arrive at structural data to be provided to the second statistical shape model.

By using the first and second statistical shape model for compression and decompression of data, the process of the transfer algorithm for transforming/converting the data in order to finally arrive at a functional form for the first patient is particularly optimized with regard to amount of data and processing time.

In a further preferred embodiment the transfer algorithm is modified and/or trained on basis of the anatomic structural data and structural data of the various patients as comprised by the first statistical shape model and the second statistical shape model, in particular in form of encoded anatomic structural data and structural data of various patients, such that the transfer algorithm, in particular using a neural network, is capable of generating structural data of the first patient being provided to the second statistical shape model.

In particular, the anatomic structural data and the functional form data of the various patients form data pairs being comprised by the first and second statistical shape model. On this basis, the transfer algorithm can be trained in order to provide individual structural data for a first patient on basis of a scan of the first patient, in particular on basis of the anatomic structural data of the first patient.

According to another embodiment the transfer algorithm uses a neural network to generate functional form data, in particular to generate structural data being decoded by the second statistical shape model to provide functional form data.

The transfer algorithm preferably uses a neural network. Thus, information as provided by the data pairs of the various different patients can be utilized by the transfer algorithm. Furthermore, additional information being extracted from further data combinations and statistical combinations can be utilized by using a neural network. Thus, the results of the transfer algorithm can advantageously be improved by using a neural network.

Furthermore, the transfer algorithm, preferably making use of a neural network, can be provided as a self-learning algorithm or a self-learning system. Thus, efficiency of the modification/learning/training process of the transfer algorithm can be increased additionally.

In one embodiment step a) comprises scanning of an extremity of the first patient, in particular of a lower leg of the first patient, to provide the anatomic structural data of the first patient. Preferably, a three-dimensional scan is executed to achieve the anatomic structural data of the first patient, in particular of the relevant extremity of the first patient.

According to one embodiment the method further comprises the following steps:

illustrating at least a visualization of a first three-dimensional structure of the anatomic structural data of the first patient, and/or illustrating at least a visualization of a second three-dimensional structure of the functional form data of the first patient.

In particular, the anatomic structural data as well as the resulting functional form data of the first patient can be visualized as three-dimensional structures and thus illustrated e.g. by a display or the like.

Thus, the patient's extremity on basis of the anatomic structural data as well as the resulting functional form data, as provided by the process preferably including the first statistical shape model, the transfer algorithm and the second statistical shape model, can be visually evaluated, e.g. by the first patient and/or the certified prosthetist/orthotist and/or the orthopaedic technician.

In another embodiment of the present invention the visualization of the first three-dimensional structure and the visualization of the second three-dimensional structure are movable relative to each other such that the first and second three-dimensional structures do not overlap each other or at least partially overlap each other.

Thus, the two resulting models can be visually compared and overlapped, e.g. for identifying necessary modifications on the provided functional form data.

According to one embodiment, after illustrating the visualization of the first three-dimensional structure and/or of the visualization of the second three-dimensional structure, user input is received for modifying the visualization of the first three-dimensional structure of the anatomic structural data and/or the visualization of the three-dimensional structure of the functional form data.

In particular, the first three-dimensional structure of the anatomic structural data and/or the second three-dimensional structure of the functional form data itself can be manually modified. Thus, the certified prosthetist/orthotist and/or the orthopaedic technician can manually and individually adapt the automatically provided functional form data additionally.

Another aspect of the present invention refers to a data processing system comprising means for carrying out the steps of the method according to the present invention. In one preferred embodiment at least one client and at least one server is provided, whereby the client is capable of sending the anatomic structural data of the first patient to the server and receiving the functional form data of the first patient from the server, and whereby the at least one server is capable of:

receiving the anatomic structural data of the first patient from the client, processing the anatomic structural data of the first patient by at least the transfer algorithm, preferably by the first statistical shape model, the transfer algorithm and the second statistical shape model, to generate functional form data of the first patient, providing functional form data of the first patient to the client.

The client can be used for gathering anatomic structural data and reviewing and/or manually modifying the resulting functional form data e.g. at a local premises of the respective certified prosthetist/orthotist and/or orthopaedic technician. In contrast thereto, extensive workloads for processing the anatomic structural data in order to provide functional form data for the first patient can be outsourced to an external server, comprising sufficient processing capacity and storage for handling of the data.

In a further aspect, the invention refers to a computer-readable medium comprising instructions which, when executed by a computer, cause the computer to carry out the steps of the method according to the present invention.

BRIEF DESCRIPTION OF THE DRAWINGS

In the following, the present invention is described in more detail by referring to the comprised figure. However, further conceivable examples of the present invention shall not be excluded thereby.

The FIGURE schematically illustrates:

FIG. 1: an exemplary flow chart of a computer-implemented method for creating a functional form.

DETAILED DESCRIPTION

According to FIG. 1, a first method step comprises a patient scan 10, in particular the scanning process of a first patient's extremity such as a lower leg in order to gather anatomic structural data ASD of the first patient. This step can be handled by a client being e.g. located at a premises of a certified prosthetist/orthotist and/or orthopaedic technician.

The anatomic structural data ASD are preferably provided to a server comprising a first statistical shape model (SSM1) 20. Furthermore, the first statistical shape model 20 is provided with anatomic structural data of a limited amount of various patients, in particular comprises encoded anatomic structural data of the limited amount of various patients.

The first statistical shape model 20 encodes the anatomic structural data ASD of the first patient to provide an encoded anatomic structural data eASD. This encoded anatomic structural data eASD represent compressed data of the anatomic structural data ASD of the first patient, preferably comprising deviations of the first patient's anatomical structural data ASD from the anatomic structural data of the limited amount of various patients. Thus, the amount of data is reduced to characteristic information, for example statistical deviations of specific landmark points of the relevant extremity.

Afterwards, the encoded anatomic structural data eASD are provided to and handled by the transfer algorithm 30, preferably using a neural network, in order to transfer the encoded anatomic structural data eASD of the first patient as comprised by the first statistical shape model 20 to structural data SD. The structural data SD are provided to the second statistical shape model 40.

The second statistical shape model 40 comprises the structural data SD of the first patient as processed by the transfer algorithm 30, as well as functional form data, preferably in form of structural data, of a limited amount of various patients. Thus, the first and second statistical shape models 20; 40 provide data pairs of the limited amount of various patients in order to modify and/or train the transfer algorithm 30 adequately. On this basis, the transfer algorithm 30, preferably using a neural network, is capable of transferring encoded anatomic structural data eASD of the first statistical shape model 30 to structural data SD of the first patient being provided to the second statistical shape model 40.

In a next step, the second statistical shape model 40 decodes the structural data SD of the first patient in order to arrive at functional form data FFD of the first patient. Thus, the transfer algorithm 30 is capable of transferring anatomic structural data ASD, in particular encoded anatomic structural data eASD, of the first patient to functional form data FFD, in particular to structural data SD, forming the basis for an individually fitting of an orthosis or prosthesis.

The functional form data FFD is preferably sent back by the server to the local client of the certified prosthetist/orthotist and/or the orthopaedic technician. Thus, large workloads can be centralized at the server, whereas the scanning process 10 for gathering data as well as the individual handling of the automatically achieved functional form (FF) 50 can be provided at a local place of the patient and/or of the certified prosthetist/orthotist and/or the orthopaedic technician.

The steps according to FIG. 1 can be summarized as follows. In a first step a patient scan 10 is performed to achieve anatomic structural data ASD of the first patient. These anatomic structural data ASD are preferably sent to the server by the local client.

In a next step a first statistical shape model 20 processes/encodes the anatomic structural data ASD of the first patient to receive encoded anatomic structural data eASD, on basis of anatomic structural data of further patients comprised by the first statistical shape model 20. This encoding process can be understood as a data compression, reducing the anatomic structural data ASD to statistical deviations or the like.

Afterwards, the transfer algorithms 30 processes the encoded anatomic structural data eASD of the first patient in order to provide structural data SD. This transformation is processed by the transfer algorithm 30, preferably using a neural network. In particular, on basis of data pairs, namely anatomic structural data and structural data, of a limited amount of patients as provided to the first and second statistical shape model 20; 40, and being compressed to encoded anatomic structural data and structural data, the transfer algorithm 30, preferably the used neural network, can be trained to provide an adequate transformation of the encoded anatomic structural data eASD of the first patient to structural data SD.

In a further step, the second statistical shape model 40 decodes the structural data SD of the first patient as received from the transfer algorithm 30 in order to finally achieve functional form data FFD. This decoding process by the second statistical shape model 40 can be understood as regeneration of data information by converting statistical deviations as represented by the structural data SD to a complete data set as represented by the functional form data FFD.

Preferably, the anatomic structural data ASD are received and processed by the server, whereby the resulting functional form data FFD is sent back to the client by the server.

Thus, after providing the functional form data FFD, a three-dimensional structure of the anatomic structural data ASD as well as of the functional form data FFD/the functional form 50 can be visualized and illustrated for the first patient and/or the certified prosthetist/orthotist and/or the orthopaedic technician, preferably by the client.

In a nutshell, the present invention provides an option to automatically generate an individualized functional form 50 on basis of the anatomic structural data ASD of a patient as provided by a usual scan of an extremity. This individual functional form 50 can be used for adequately fitting an orthosis or prosthesis to a first patient.

Further, by utilizing statistical shape models 20; 40 for intermediate encoding and decoding of the data, the amount of data to be processed can be reduced to significant and characteristic data sets, and reproduced afterwards without relevant losses of information in order to arrive at a suitable individualized functional form 50.

Moreover, by processing data by a transfer algorithm 30, preferably using a neural network, the efficiency of the process and the accuracy of the resulting functional form data FFD are advantageously improved.

The invention claimed is:

1. A computer-implemented method for creating a functional form, representing an adapted geometry of a patient's anatomy in order to fit an orthosis or prosthesis to a first patient, comprising the following steps:
   a) receiving anatomic structural data of the first patient from a patient scan;
   b) applying a transfer algorithm to generate functional form data for the first patient, wherein applying the transfer algorithm comprises:
      b1) encoding the anatomic structural data using a first statistical shape model to provide encoded structural data,
      b2) using a neural network trained to map the encoded anatomical structural data from the first statistical shape model to structural data compatible with the second statistical shape model to transfer the encoded anatomical structural data to structural data, and
      b3) decoding the structural data using a second statistical model to generate the functional form data;
   whereby the functional form data forms the basis on which an individualized orthosis or prosthesis is manufactured.

2. The method according to claim 1, wherein the encoded structural data produced by the first statistical shape model is of a reduced size as compared to the anatomic structural data.

3. The method according to claim 1, wherein the first statistical shape model encodes the anatomic structural data in form of deviations of the anatomic structural data (ASD) of the first patient from anatomic structural data of a limited amount of various patients as comprised by the first statistical shape model.

4. The method according to claim 3, wherein the deviations are specified for a predetermined number of characteristic landmark points of an extremity of the first patient.

5. The method according to claim 1, wherein the second statistical shape model decodes the structural data of the first patient representing deviations from functional form data of a limited amount of various patients as comprised by the second statistical shape model to provide functional form data for the first patient.

6. The method according to claim 1, wherein the transfer algorithm is modified or trained on a basis of the anatomic structural data and functional form data of various patients as comprised by the first statistical shape model and the second statistical shape model such that the transfer algorithm is capable of generating structural data of the first patient being provided to the second statistical shape model.

7. The method according to claim 1, wherein step a) comprises scanning of an extremity of the first patient, in particular of a lower leg of the first patient, to provide the anatomic structural data of the first patient.

8. The method according to claim 1, further comprising at least one of:

illustrating at least a visualization of a first three-dimensional structure of the anatomic structural data of the first patient, or illustrating at least a visualization of a second three-dimensional structure of the functional form data of the first patient.

9. The method according to claim 8, wherein the visualization of the first three-dimensional structure and the visualization of the second three-dimensional structure are movable relative to each other such that the first and second three-dimensional structures do not overlap each other or at least partially overlap each other.

10. The method according to claim 8, wherein, after illustrating the visualization of the first three-dimensional structure and/or of the visualization of the second three-dimensional structure, receiving user input for modifying the visualization of the first three-dimensional structure of the anatomic structural data or the visualization of the three-dimensional structure of the functional form data.

11. A data processing system comprising:

one or more non-transitory computer-readable mediums storing instructions for carrying out the steps of the method of claim 1, and one or more processors configured to execute the instructions.

12. The data processing system according to claim 11, wherein the data processing system comprise at least one client and at least one server, whereby the client is capable of sending the anatomic structural data of the first patient to the server and receiving the functional form data of the first patient from the server, and whereby at least one server is capable of:

receiving the anatomic structural data of the first patient from the client, processing the anatomic structural data of the first patient by at least the transfer algorithm, preferably by the first statistical shape model, the transfer algorithm and the second statistical shape model, to generate functional form data of the first patient, providing functional form data of the first patient to the client.

13. A non-transitory computer-readable medium comprising instructions which, when executed by a computer, cause the computer to carry out the steps of the method of claim 1.

14. The method of claim 1, further comprising manufacturing the individualized orthosis or prosthesis based on the functional form data.

* * * * *